United States Patent [19]
Samoto et al.

[11] Patent Number: 5,597,607
[45] Date of Patent: Jan. 28, 1997

[54] PROCESS FOR PREPARING FRACTIONATED SOYBEAN PROTEINS AND FOODS USING THE SAME

[75] Inventors: Masahiko Samoto; Takeshi Akasaka, both of Tsukuba-gun; Hiroyuki Mori, Abiko, all of Japan

[73] Assignee: Fuji Oil Company, Limited, Osaka-fu, Japan

[21] Appl. No.: 364,102

[22] Filed: Dec. 27, 1994

[30] Foreign Application Priority Data

Jan. 7, 1994 [JP] Japan .................................. 6-000620
Nov. 22, 1994 [JP] Japan .................................. 6-288425

[51] Int. Cl.$^6$ .................. A23J 1/14; A23J 3/16; A23L 1/20
[52] U.S. Cl. .................................. 426/656; 530/378
[58] Field of Search .......................... 426/656; 530/378

[56] References Cited

FOREIGN PATENT DOCUMENTS 0072094 2/1983 European Pat. Off. .

OTHER PUBLICATIONS

Ogawa et al J. Nutri. Sci Vitaminol., 37, 555–565, (1991).
Thanh et al J. Agric. Food Chem. vol. 24, No. 6 pp. 1117–1121 (1976).
Sato et al Phyfochemistry, vol. 23, No. 8 pp. 1523–1526, 1984.
Abstract of JP–52–035739, NODA Inst Sci Res, "Soyabean 7S Protein Production by Dispersing Soyaben GLobulin in a Solution Containing Sodium Chloride or Potassium Chloride", Sep. 10, 1977.
Abstract of JP–5–043597, Nagano et al, "Method for Fractioning 7S Protein", Feb. 23, 1993.
Abstract of JP–55–124457, Koshiyama et al., "Preparation of 7S Protein", Sep. 25, 1980.
Anderson et al., "Extraction of Soybean Meal Proteins with Salt Solutions at pH 4.5", J. Agr. Food Chem, vol. 21, No. 2, pp. 251–254, 1973.
Iwabuchi et al., "Determination of GLycinin and β–Conglycinin in Soybean Proteins by Immunological Methods", J. Agr. Food Chem. vol. 35, No. 2, pp. 200–205, 1987.

Primary Examiner—Esther M. Kepplinger
Assistant Examiner—Choon P. Koh
Attorney, Agent, or Firm—Wenderoth, Lind & Ponack

[57] ABSTRACT

A novel, efficient and simple process for preparing low-allergenic fractionated soybean proteins by treating soybean proteins under acidic conditions with an aqueous solution in which a salt is dissolved to selectively concentrate Gly m Bd 30k in a precipitation fraction and collecting a supernatant fraction.

11 Claims, 3 Drawing Sheets

PROCESS FOR PREPARING FRACTIONATED SOYBEAN PROTEINS AND FOODS USING THE SAME

FIELD OF THE INVENTION

The present invention relates to a process for preparing fractionated soybean proteins which are low-allergenic and have improved color tone (e.g., brightness, clarity), flavor, taste and gel strength. The present invention also relates to low-allergenic foods using the proteins.

BACKGROUND OF THE INVENTION

Recently, allergic patients such as patients with atopic dermatitis have been increased. As for foods, proteins contained in egg white, soybean and milk are recognized as the three main allergens. Then, so-called an elimination diet is introduced as a symptomatic treatment. However, of the above allergens, soybean proteins are widely contained in Japanese traditional foods such as soy sauce, miso (fermented soybean paste), tofu (soybean curd), aburaage (fried tofu), koridofu (freeze-dried tofu) and yuba (membrane-like soybean protein food) as well as in other foods which contain soybean proteins as a part of their raw materials. Moreover, recently, variations of foods utilizing functional properties of soybean proteins, such as emulsification, gel-formation, film-formation, water-retention, viscosity, foaming and the like have increased, which makes selection of the elimination diet difficult.

Ogawa et al. (Biosci. Biotech. Biochem., 57:1030 (1993)) have identified a soybean protein component having a high reactivity to IgE antibody from an atopic patient against soybean as Gly m Bd 30k which is a fraction showing a 34 kDa band in SDS-PAGE electrophoresis. In addition, they have also found that 7S fraction contains a large amount of Gly m Bd 30k, while 11S fraction and whey fraction fractionated by the method of Than and Shibasaki (J. Agric. Food Chem., 24:1117–1121(1976)) scarcely contains it.

However, it is very difficult to separate and remove Gly m Bd 30k from 7S fraction by a known method in an industrial scale. On the other hand, even when proteins are collected only from 11S fraction and whey fraction, the sum of them amounts to only 30 to 40% (25 to 30% from 11S fraction alone) of whole soybean milk proteins. Thus, there is a problem that a yield of low-allergenic soybean proteins is low. Moreover, there is a problem of productivity that a delicate pH adjustment of soybean milk and a long-term treatment at a low temperature are needed in fractionation of 7 S fraction and 11 S fraction, or a problem that functional properties of soybean proteins are considerably changed when 7 S protein is absent.

Although, afterwards, Ogawa et. al. have re-named Gly m Bd 30k as "Gly m I", in the present specification, the protein is referred to as "Gly m Bd 30k" or "allergenic protein".

OBJECTS OF THE INVENTION

The present inventors have studied intensively so as to prepare low-allergenic soybean proteins from which almost all Gly m Bd 30k has been removed, efficiently, that is, in a high yield, by a simple process. As a result, regarding main soybean storage proteins (β-coglycinin and glycinin) and Gly m Bd 30k, it has been found that there is a difference between dissolution and precipitation behavior of proteins in the presence of a dissolved salt at acidic pH, and that the above problems can be solved by utilizing this difference without requiring fractionation of 7S and 11S fractions.

In addition, it has also been found that a soybean protein containing a reduced amount of Gly m Bd 30k thus obtained has improved color, flavor, taste and gel strength in comparison with conventional soybean proteins and therefore wide use which is not limit to for soybean protein allergic is expected. Furthermore, it has also been found that the soybean protein show selective precipitation property at a specific acidic pH range even with a small amount of a salt.

The main object of the present invention is to provide a novel, efficient and simple process for preparing low-allergenic soybean proteins of which Gly m Bd 30k content is minimized.

This object as well as other objects and advantages of the present invention will become apparent to those skilled in the art from the following description with reference to the accompanying drawings.

BRIEF DESCRIPTION OF THE DRAWINGS

In FIG. 1, Nos. 1 to 12 correspond to Sample Nos. to 12 in Table 1 and the Comparative Example. "Whole" means the raw soybean milk used as the raw material in Example 1.

SUMMARY OF THE INVENTION

Figure 1:
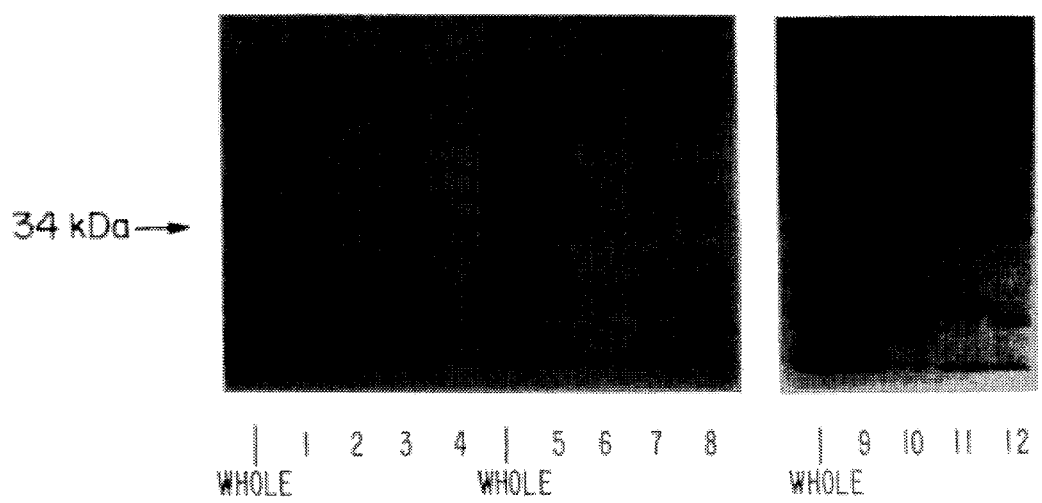
FIG. 1 is a photograph showing SDS-PAGE electrophoresis patterns of the products in Example 1 and Comparative Example.

According to the present invention, there is provided a process for preparing fractionated soybean proteins which comprises treating soybean proteins under acidic conditions with an aqueous salt solution, selectively concentrating Gly m Bd 30k in a precipitation fraction and collecting a supernatant fraction.

The present invention also provides foods comprising the soybean proteins obtained by the process of the present invention.

DETAILED DESCRIPTION OF THE INVENTION

The process of the present invention comprises treating soybean proteins with an aqueous salt solution under acidic conditions, selectively concentrating Gly m Bd 30k in a precipitation fraction and collecting a supernatant fraction.

The treatment under acidic conditions in the present invention may be any treatment where the soybean proteins are exposed to an acidic aqueous salt solution. In a preferred embodiment, a precipitation fraction is obtained from an aqueous extract of soybean proteins, or a soluble fraction is separated from proteins precipitated with an acid.

If the treatment under acidic conditions is not carried out, separation hardly takes place even under high gravity and a large amount of the allergenic proteins remain in a supernatant, while a small amount of a precipitation fraction is formed. In general, when the treatment is carried out under acidic conditions of higher than pH 5, selective precipitation of the allergenic protein in the presence of a dissolved salt is not effectively improved.

As the salt to be used, salts of alkaline metals, such as sodium and potassium are suitable for the present invention. Salts of alkaline earth metals are not suitable for obtaining soybean proteins in a high yield at a high salt concentration because they tend to bind to the main storage proteins. However, when a salt concentration of an alkaline earth metal is low, for example, 100 mM or lower, such a problem hardly occurs and, therefore, alkaline earth metal salts can be used.

Similar to the order of so-called Hofmeister's series of the counter ions, selectivity for enhancing precipitation property of the allergenic protein is decreased in the order of salts having polyvalent acidic radicals such as citrates, tartarates and sulfates; acetates; and then chlorides. Therefore, when a salt having polyvalent (divalent or higher) acidic radicals or an acetate is used, the amount thereof may be smaller in comparison with a chloride. As for sodium salts, for example, when 0.3M (molar concentration) sodium sulfate (ionic strength: 0.9) and 1M sodium chloride (ionic strength: 1.0) are used at the pH range of 3.5 to 4.7, even if almost the same amount of proteins are contained in a supernatant fraction, the allergenic protein is more effectively removed from the proteins in the supernatant fraction with 0.3M sodium sulfate, although both ion strengths are almost the same. Furthermore, 0.3M Sodium sulfate is more effective than 4M sodium chloride (ionic strength: 4.0) to remove the allergenic protein.

As a salt concentration increases, selective precipitation property of the allergenic protein increases. However, when the salt concentration reaches a certain level, precipitation property of main soybean storage proteins also increases and therefore the selectivity for precipitation becomes lower (that is, a yield of low-allergenic proteins in the supernatant fraction decreases). Thus, it is desired that the salt concentration as the ionic strength is 5 or less, preferably, 4 or less.

On the contrary, when the salt concentration is low, main soybean storage proteins are also precipitated in their isoelectric point range, that is, in an acidic range of pH 3.5 to 5.0, normally 3.8 to 4.7, which makes selective precipitation of the allergenic protein difficult. In such a case, it is preferred to use an acetate or a salt having polyvalent acidic radicals in a concentration of 90 mM or higher, more preferably 150 mM or higher, or to use a chloride in a concentration of 1,200 mM or higher, more preferably, 2,000 mM or higher in the treatment. However, in the case that a chloride is used in combination with an acetate or a salt having polyvalent acidic radicals, the concentrations of the salts can be lower than the above lower limits because the respective salts are used in concentrations divided in proportional to their activities (the same shall apply hereinafter).

As the salt concentration is lower, selective precipitation property of the allergenic protein is decreased. However, in a pH range lower than isoelectric points of so-called soybean storage proteins, that is, in a range of pH 4.0 or lower, normally 3.8 or lower, precipitation property of the main storage proteins is also low (high solubility) and therefore such a preferred effects are obtained that the allergic protein can be precipitated selectively with a smaller amount of the salt than that described above and thereby a desaltation step can be omitted.

However, in general, the pH of the treatment should not be lower than 2.0 because proteins are denatured at an extremely low pH and, depending upon a particular use, they cannot be practically used. In addition, in view of resistance to acids and corrosion of production equipments, pH of 3.5 to 5.0, normally 3.8 to 4.7 may be selected. Where the pH is 2.0 to 4.0, more preferably, 2.5 to 3.8, the suitable concentration for an acetate or a salt having polyvalent acidic radicals is 3 mM or higher, more preferably, 20 mM or higher and the suitable concentration for a chloride is 600 mM or higher, more preferably, 900 mM or higher.

Examples of soybean proteins to be used as a raw material in the present invention include soybean milk extracted from soybeans or defatted soybeans, acid-precipitated soybean proteins prepared by adjusting pH of such soybean milk to its isoelectric point, so-called isolated soybean proteins prepared by neutralizing acid-precipitated proteins and the like. Defatted soybean proteins with low heat history are useful to obtain the desired end proteins in a high yield. In addition, when proteins from soybeans which are not stale are used, a high yield of the desired end proteins is readily and stably maintained.

However, even when denatured proteins with heat history to some extent or raw material proteins from so-called old-crop soybeans are used, the desired end proteins can be obtained in a high or stable yield by using a reducing agent such as salts, for example, $NaHSO_3$, cysteine, and other S—S bond cleaving agents and the like, or by treating soybeans or soybean milk under electrically reducing conditions.

An aqueous extract of soybean proteins can be prepared, for example, by adding a salt to defatted soybean milk [a supernatant prepared by extracting fats and oils from milled soybeans with hexane, adding water to the residue, adjusting the pH of the mixture to neutral or a slight alkaline region if desired and removing "okara (residue after separating soybean milk)"]; by adding water to water-soluble isolated soybean proteins and then adding a salt thereto; or by adding water and an alkaline or acid to acid-precipitated soybean proteins to dissolve them and then adding a salt thereto. Alternatively, a salt can be firstly dissolved, followed by extraction. The pH of the aqueous extract is neutral or slightly alkaline, preferably pH 6.5 or higher, more preferably pH 7.0 or higher, or acidic such as pH 2.0 to 4.0, preferably pH 2.5 to 3.8. The solids content of the aqueous extract is selected from the range of about 1 to 20% by weight in an aqueous medium. The aqueous medium may be water containing the above salt and optionally an emulsifier.

In the present invention, pH can be adjusted by a conventional method such as addition of an acid, for example, hydrochloric acid, sulfuric acid, phosphoric acid, citric acid, or a base, for example, sodium hydroxide, potassium hydroxide, calcium hydroxide.

The treatment under acidic conditions of the present invention is conducted, for example, at 0° to 50° C. for 1 minute to 3 hours.

Thus, according to the present invention, the allergenic protein Gly m Bd 30k can be selectively concentrated in a precipitation fraction obtained by the above treatment under acidic conditions. A supernatant fraction from which the precipitation fraction is separated is collected according to a conventional method such as centrifugation, filtration, decondition and the like as a fraction containing soybean proteins or fractionated soybean proteins which are low-allergenic, or have excellent color, flavor, taste, gel formation ability and the like. This fraction can be used as it is without any additional treatment as a raw material of processed soybean foods such as tofu (soybean curd), aburaage (fried tofu), koridofu (freeze-dried tofu), yuba (membrane-like soybean protein food), soybean milk, miso (fermented soybean paste), soy sauce, textured soybean protein foods and the like. Alternatively, according to a particular purpose, this fraction can be subjected to an additional treatment such as neutralization, desalting by electrical dialysis or the like, heat sterilization, or drying, for example, freeze-drying, spray-drying, vacuum-drying, hot-air-drying. Optionally, after desalting (when a small amount of the salt is used, desaltation is not needed), adjusting pH to about the isoelectric point and then removing whey, this fraction can be used for the production of soybean protein foods in a similar manner as so-called acid-precipitated soybean proteins and isolated soybean proteins, for example, the production of fibrous or membrane proteins or additives for meat, fowl meat and/or fish meat paste products. These foods are not only useful as low-allergenic foods or allergen-eliminated foods, but also are foods having bland flavor, taste and color tone.

The following Examples and Comparative Example further illustrate the present invention in detail. However, they are not to be construed to limit the scope of the present invention.

EXAMPLE 1 AND THE COMPARATIVE EXAMPLE

To defatted soybeans prepared from new-crop soybeans (100 g) was added water (1,500 ml) and the pH of the mixture was adjusted to 7.5 with addition of 1N NaOH. The mixture was stirred at room temperature for 3 hours to carry out extraction followed by removal of "okara" component by centrifugation to obtain defatted soybean milk.

The soybean milk thus obtained is hereinafter referred to as "raw soybean milk".

The raw soybean milk was divided into 40 ml portions and sodium chloride or sodium sulfate in a concentration as shown in Table 1 was added to each portion to dissolve the salt. Then, the mixture was centrifuged at the same pH at 200,000 g for 50 minutes, or the mixture was adjusted to pH 4.5 with aqueous HCl followed by centrifugation at 10,000 g for 10 minutes to obtain supernatant and precipitation fractions of each portion (Sample Nos. 1 to 12). Protein contents (determined by biuret method) of the supernatant fractions are shown in Table 1 together with the recoveries calculated by taking 1.16 g of proteins in 40 ml of the raw soybean milk as 100%. All the recoveries were considerably higher than those of 11S protein (glycinin) obtained by separating so-called 7S protein (β-conglycinin) therefrom.

TABLE 1

| Salt added to soybean milk and concentration | | pH at centrifugation | Sample No. sup. | Sample No. ppt. | Protein content in sup. (and recovery) |
|---|---|---|---|---|---|
| NaCl | 1.0M | 7.5 | 1 | 2 | 1.03 g (79%) |
| NaCl | 4.0M | 7.5 | 3 | 4 | 1.02 g (68%) |
| NaCl | 1.0M | 4.5 | 5 | 6 | 0.92 g (79%) |
| NaCl | 4.0M | 4.5 | 7 | 8 | 0.79 g (68%) |
| Na$_2$SO$_4$ | 0.3M | 4.5 | 9 | 10 | 0.91 g (78%) |
| Na$_2$SO$_4$ | 1.0M | 4.5 | 11 | 12 | 0.80 g (69%) |

Figure 2:
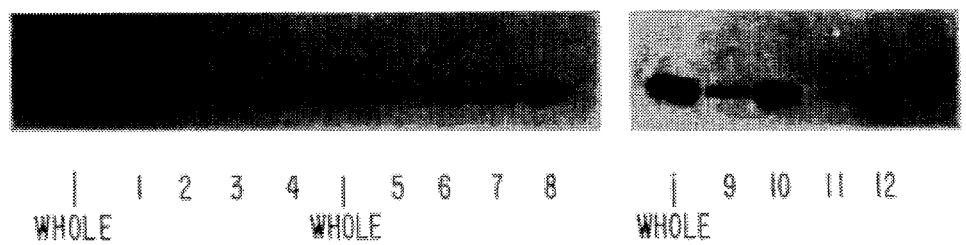
FIG. 2 shows immunoblots of Example 1 and Comparative. Example. The immunoblots were obtained by detecting fluorescence with a X-ray film.

SDS-PAGE Electrophoresis (12% gel, width 1 mm) was performed in order to investigate the content of the allergenic protein Gly m Bd 30k in the raw soybean milk as well as in the supernatant and the precipitation fractions (Sample Nos. 1 to 12) by an immunological method. The results are shown in FIG. 1. In the case of the raw soybean milk (indicated by "whole" in FIG. 1), the protein was applied in an amount of 10 μg and, for the other fractions, the amounts of proteins to be applied were proportional to this amount according to the amounts of proteins separated. Gly m Bd 30k migrated about 34 kDa in FIG. 1. The SDS-PAGE was transferred to a nitrocellulose membrane (manufactured by BIO RAD) and the protein was detected (by detecting fluorescence due to peroxidase using X-ray film) by using a monoclonal antibody specific to Gly m 30k and ECL immunodetection reagents (manufactured by Amersham Institute). The results are shown in FIG. 2.

As seen from FIG. 1, in comparison with sodium chloride, when sodium sulfate was used, separation and selectivity properties of the allergenic protein were more improved and the amounts of β-conglycinin and glycinin in the precipitation fraction were smaller. And, as seen from FIG. 2, the effect of removal of the allergenic protein is improved in the order of Sample Nos. 11, 9, 7, and 5. No allergen was detected in Sample No. 11. On the other hand, a small amount of the allergenic protein remained in Sample No. 5, though a considerable amount of the allergenic protein was removed.

EXAMPLE 2

To raw soybean milk prepared according to the same manner as described in Example 1 was added a salt selected from the group consisting of tri-sodium citrate, sodium tartarate, sodium sulfate, sodium acetate and sodium chloride in the concentration shown in Table 2 and the salt was dissolved. After adjusting the pH of the mixture to 4.5 with a hydrochloric acid solution, the supernatant fraction and the precipitation fraction were obtained separately by centrifugation at 10,000 g for 10 minutes. Then, the protein content in each fraction was determined. The recoveries of the proteins are shown in Table 2. Immunoblots performed according to the same manner as Example 1 indicated that the amount of the allergenic protein in the supernatant fraction decreased by any one of the salts used, and that the amount of the allergenic protein remained in the supernatant fraction obtained by using 0.2M sodium sulfate was almost the same as that obtained by using 3.0M sodium chloride.

TABLE 2

| Salt concentration | | Recovery of protein in supernatant fraction |
|---|---|---|
| Trisodium citrate | 1.0M | 72% |
| Sodium tartarate | 1.5M | 61% |
| Sodium sulfate | 1.5M | 65% |
| Sodium sulfate | 0.75M | 75% |
| Sodium sulfate | 0.5M | 77% |
| Sodium sulfate | 0.2M | 81% |
| Sodium acetate | 3.0M | 73% |
| NaCl | 3.0M | 79% |

EXAMPLE 3

To raw soybean milk prepared according to the same manner as described in Example 1 was added sodium sulfate at a concentration of 1.0M. The salt was dissolved and the mixture was acidified to pH 4.5 with a hydrochloric acid solution. Then, the precipitation fraction was removed from the supernatant fraction by centrifugation at 10,000 g for 10 minutes. After adjusting the pH of the supernatant fraction to 7.0 with sodium hydroxide, the fraction was desalted by electric dialysis and then freeze-dried to obtain a dried low-allergenic soybean protein.

EXAMPLE 4

According to the same manner as described in Example 3, a dried low-allergenic soybean protein was obtained except that old-crop soybeans were used with or without addition of 10 mM sodium hydrogen sulfite as a reducing agent to the extract from defatted soybeans. The recovery of the proteins into the supernatant fraction based on the raw soybean milk was 70% when the reducing agent was used. On the other hand, the recovery was 63%, when the reducing agent was not used.

EXAMPLE 5

Raw soybean milk prepared according to the same manner as described in Example 1 was adjusted to pH 4.5 with hydrochloric acid. Then, proteins were precipitated at the isoelectric point and whey components were removed by centrifugation to obtain precipitated soybean proteins. To the curd (101 g, water content 58%) was added a solution of sodium sulfate at a concentration of 1M to obtain a mixture (5 liters). The mixture was stirred and a soluble fraction was collected by centrifugation. For the precipitation fraction, this operation was repeated once again. The combined soluble fraction was neutralized with sodium hydroxide and then its ionic strength was lowered to about 0.03 by electric dialysis. The fraction was heat-sterilized and spray-dried to obtain isolated soybean proteins. The recovery of the proteins was 58% based on the whole soybean milk proteins.

In addition, according to the same manner as described above, the isolated soybean proteins were prepared except that 1.5M sodium chloride or 1.0M sodium chloride was used instead of 1M sodium sulfate. In these cases, the recovery of the proteins based on the proteins of raw soybean milk was 48% for 1.5M sodium chloride and 52% for 1.0M sodium chloride.

As another comparison, acid-precipitated soybean proteins were prepared according to the same manner as described about without addition of the salt and without desaltation. They were neutralized with sodium hydroxide, heat-sterilized and spray-dried to obtain isolated soybean proteins.

As shown in Table 3, four kinds of pastes containing 17% of isolated soybean proteins were prepared, filled into plastic casings having folding width of 37 mm, heated at 80° C. for 30 minutes to obtain gels. Organoleptic evaluation and measurement of breaking strength of the gels with Rheoner (manufactured by Yamaden) were carried out. 20 Panelist carried out the organoleptic evaluation of quality were by scoring with respect to three items according to the following criteria, i.e., color: from bright/10 points to dark/1 point; clearness: from clear/10 points to opaque/1 points; and flavor and taste: tasteless/10 points to bad/1 points. The results are shown in Table 3 by the average of the score. As seen from Table 3, the gel treated with 1M sodium sulfate showed very excellent results with respect to all the items of color, clearness and flavor and taste. It also showed the strongest breaking strength and strong gel formation ability. The gel treated with 1.5M sodium chloride showed considerably better results in comparison with the gel treated with 1.0M sodium chloride.

TABLE 3

| Salt added | Conc. | Color | Clearness | Taste | Break strength |
|---|---|---|---|---|---|
| Na$_2$SO$_4$ | 1.0M | 9.3 | 9.7 | 8.9 | 754 |
| NaCl | 1.5M | 7.9 | 8.7 | 8.1 | 645 |
| NaCl | 1.0M | 6.9 | 8.7 | 7.0 | 550 |
| Without addition | | 4.5 | 4.0 | 5.1 | 345 |

TABLE 3-continued

| Salt added | Conc. | Color | Clearness | Taste | Break strength |
|---|---|---|---|---|---|
| of salt and desalting | | | | | |

EXAMPLE 6

To a curd (101 g) of an acid-precipitated soybean protein prepared according to the same manner as Example 5 was added a sodium sulfate solution in such a concentration that, sodium sulfate became 0.03M, when hydrochloric acid was added to adjust the pH to 3.0. After extraction for 30 minutes, the precipitation was removed by centrifugation at 5,000 g for 10 minutes and the pH of the supernatant was adjusted to 4.5. Then, the precipitation was collected by centrifugation. To the precipitation were added water and 1N sodium hydroxide to neutralize it and then it was heat-sterilized and spray-dried to prepare isolated soybean proteins. The recovery of the isolated soybean proteins was 33% based on the whole soybean milk proteins. The results obtained by evaluation according to the same manner as Example 5 are shown in Table 4.

TABLE 4

| Color | Clearness | Taste | Break strength (g × cm) |
|---|---|---|---|
| 7.2 | 8.8 | 8.2 | 632 |

EXAMPLE 7

To raw soybean milk prepared according to the same manner as Example 1 was added sodium sulfate or tri-sodium citrate was added in a concentration of 5 mM. The pH was adjusted to 3.0 with hydrochloric acid and the precipitation fraction was removed by centrifugation at 5,000 g for 10 minutes. The pH of the supernatant fraction was adjusted to 4.5 with sodium hydroxide to cause so-called isoelectric precipitation and the whey components were removed by centrifugation to obtain a curd. Water was added to the curd and the mixture was neutralized with sodium hydroxide, heat-sterilized and spray-dried to prepare isolated soybean proteins. The recovery of the proteins was 63% based on the whole soybean milk proteins.

According to the same manner, the preparation was repeated by using sodium chloride instead of sodium sulfate or sodium tri-citrate, or without using them. The protein recovery of the former was 82% and that of the latter was 86%.

These four kinds of soybean proteins were evaluated for their qualities according to the same manner as described above. The results are showed in Table 5. The proteins obtained by treatment with 5 mM sodium sulfate and 5 mM sodium citrate showed excellent results with respect to all items, i.e., color, clearness and flavor and taste, and had strong breaking strengths showing strong gel forming ability.

TABLE 5

| Salt | Concentration | Color | Clearness | Taste | Break strength (g × cm) |
|---|---|---|---|---|---|
| Na$_2$SO$_4$ | 5 mM | 6.5 | 7.2 | 7.5 | 645 |
| Na-citrate | 5 mM | 7.0 | 6.1 | 7.3 | 429 |

TABLE 5-continued

| Salt | Concentration | Color | Clearness | Taste | Break strength (g × cm) |
|---|---|---|---|---|---|
| NaCl | 5 mM | 4.7 | 4.3 | 5.6 | 368 |
| Without addition of salt and desalting | | 4.0 | 4.5 | 5.6 | 321 |

EXAMPLE 8

To raw soybean milk prepared according to the same manner as described in Example 1 was added sodium sulfate in the concentration as shown in Table 6 and the mixture was stirred and adjusted to pH 2.8 with hydrochloric acid. The mixture was centrifuged at 10,000 g for 10 minutes to obtain a supernatant fraction and the protein content thereof was determined by Kjeldahl method. The solubility ratio in Table 6 were calculated by taking the whole protein content in the raw soybean milk as 100%. The proteins contained in the supernatant were separated into the constituent proteins by SDS-electrophoresis. After subjecting to CBB protein stain, the peak areas were measured by densitometry. The solubility ratio of respective constituent proteins were calculated by taking the total peak areas of these constituent proteins in the raw soybean milk as 100%. The solubility ratio of respective constituent proteins is also shown in Table 6 and FIG. 3.

TABLE 6

| Solubility ratio | Raw soybean milk | Concentration of $Na_2SO_4$ in soybean milk (mM) | | | | | |
|---|---|---|---|---|---|---|---|
| | | 0 | 1 | 5 | 10 | 20 | 30 | 100 |
| Protein content in supernatant SDS-electrophoresis | 100% | 95% | 91% | 85% | 72% | 68% | 60% | 62% |
| 7S | 100% | 95% | 92% | 76% | 73% | 71% | 70% | 66% |
| 11S | 100% | 90% | 90% | 82% | 75% | 67% | 59% | 74% |
| Gly m Bd 30k | 100% | 89% | 87% | 66% | 41% | 22% | 12% | 8% |

Figure 3:
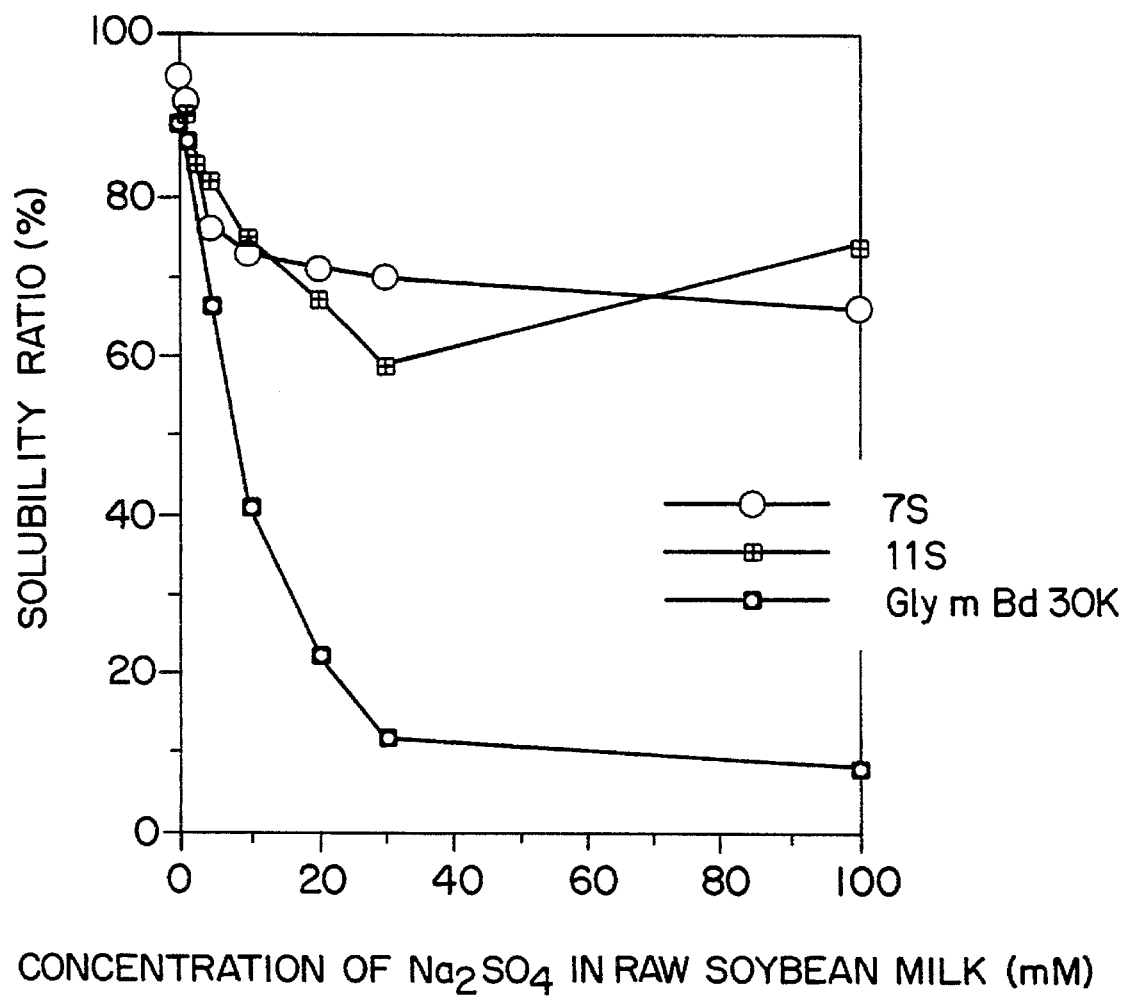
FIG. 3 is a graph showing solubility ratios of 7S, 11S and Gly m Bd 30k at various concentrations of sodium sulfate.

As seen from Table 6 and FIG. 3, selective precipitation property of Gly m Bd 30k from 7S protein and 11S protein at pH 2.8 is not so significant, when the concentration of sodium sulfate is about 1 mM. On the other hand, when the concentration of sodium sulfate is about 5 mM, certain difference is recognized and, when the concentration is higher than about 20 mM, significant difference is observed.

As described hereinabove, according to the present invention, low-allergenic fractionated soybean proteins can be obtained in a high yield by a simple method. The color, clearness, flavor and taste and gel strength of the fractionated soybean proteins are remarkably improved. In particular, when a salt having a polyvalent acidic radical is used, these properties can be further improved. In addition, the fractionated soybean proteins of the present invention can be used as sources of good proteins for allergic patients against soybeans to whom supply of the proteins has been difficult by elimination diets.

What is claimed is:

1. A process for preparing fractionated soybean proteins which comprises treating soybean proteins under acidic conditions at a pH of therewith 2–4.7 with an aqueous solution in which an alkaline metal or an alkaline earth metal salt is dissolved to selectively concentrate Gly m Bd 30k in a precipitation fraction without fractionation of 7S and 11S fractions and collecting a supernatant fraction.

2. A process according to claim 1, wherein the soybean proteins to be treated under acidic conditions is an aqueous extract of soybean proteins.

3. A process according to claim 1, wherein the treatment is carried out by extracting a soluble fraction from acid-precipitated soybean proteins.

4. A process according to claim 1, wherein the treatment is carried out at pH of 3.8 to 4.7.

5. A process according to claim 1, wherein the treatment is carried out at pH 3.5 to 4.7 and a salt concentration of 90 mM or higher in the case of a salt having a polyvalent acidic radical or an acetate, or 1,200 mM or higher in the case of a chloride.

6. A process according to claim 1, wherein the treatment is carried out at pH 2.0 to 4.0 and a salt concentration of 3 mM or higher in the case of a salt having a polyvalent acidic radical, or 600 mM or higher in the case of a chloride.

7. A process according to claim 1, wherein the treatment is carried out at pH 2.0 to 4.0 and a salt concentration of 20 mM or higher in the case of a salt having a polyvalent acidic radical, or 900 mM or higher in the case of a chloride.

8. A process according to claim 1, wherein the soybean proteins to be treated is treated with a reducing agent or treated under electrically reducing conditions prior to collecting the supernatant fraction.

9. A process according to claim 1, wherein the supernatant fraction collected is neutralized, desalted, heat-sterilized or dried, or is subjected to removal of whey.

10. A food comprising the fractionated soybean proteins obtained by the process according to claim 1.

11. A food prepared by the process of claim 9 which is a low-allergenic food for allergic patients against soybeans.

* * * * *